US005458869A

United States Patent [19]
Berg et al.

[11] Patent Number: 5,458,869
[45] Date of Patent: Oct. 17, 1995

[54] MULTINUCLEAR COMPLEXES FOR X-RAY IMAGING

[75] Inventors: Arne Berg, Blommenholm, Norway; Torsten Almén, Malmö, Sweden; Klaus D. Krautwurst, Stabbek, Norway; Sook-Hui Kim, Mountain View, Calif.; Pål Rongved, Hellvik, Norway; Jo Klaveness; Harald Dugstad, both of Oslo, Norway

[73] Assignee: Nycomed Salutar Inc., Sunnyvale, Calif.

[21] Appl. No.: 927,484

[22] PCT Filed: Mar. 27, 1991

[86] PCT No.: PCT/EP91/00587

§ 371 Date: Nov. 24, 1992

§ 102(e) Date: Nov. 24, 1992

[87] PCT Pub. No.: WO91/14460

PCT Pub. Date: Oct. 3, 1991

[30] Foreign Application Priority Data

Mar. 28, 1990 [GB] United Kingdom ............... 900677

[51] Int. Cl.$^6$ ...................................................... A61K 49/04
[52] U.S. Cl. ................... 424/9.42; 556/1; 556/28; 556/50; 514/184; 514/492; 514/836
[58] Field of Search ....................... 424/4; 556/28, 556/50, 1; 514/492, 184, 836

[56] References Cited

U.S. PATENT DOCUMENTS

| | | | |
|---|---|---|---|
| 3,763,188 | 10/1973 | Krespan | 260/338 |
| 3,860,611 | 1/1975 | Krespan | 260/338 |
| 3,952,015 | 4/1976 | Krespan | 260/338 |
| 4,079,124 | 3/1978 | Winchell | 424/4 |
| 4,176,173 | 11/1979 | Winchell et al. | 424/5 |
| 4,647,447 | 3/1987 | Gries et al. | 424/9 |
| 4,795,698 | 1/1989 | Owen et al. | 435/4 |

FOREIGN PATENT DOCUMENTS

| | | |
|---|---|---|
| 2348699 | 11/1977 | France. |
| 89/10372 | 11/1989 | WIPO. |
| 90/03190 | 5/1990 | WIPO. |
| 91/14460 | 10/1991 | WIPO. |

OTHER PUBLICATIONS

Cotton, FA, Polyhedron 5(½):3–14 (1986).
Wang, B. et al., J. American Chemical Society 108:6059–6060 (1986).
Shibahara et al., J. American Chemical Society 108:2757–2758 (1986).
Siedle et al., Aryl-Substituted Molecular Metal Oxide Clusters, J. Am. Chem. Soc., (1986), 108, pp. 6430–6431.
Novak et al., Tungsten (V) Complexes of Ethylenediaminetetraacetic Acid, med. Chem. (1974), vol. 36, pp. 1061–1065.
Saito et al., Synthesis of ... for Superconducting Chevrel Phases, J. Am. Chem. Soc., (1988), 110, 1646–1647.
Shibahara et al., Preparation of Triangular (IV) Aqua Ion, . . ., J. Am. Chem. Soc. (1986), 108, 2757–2758.
Ott et al., Di–µ–oxo, µ–Oxo–sulfido, and . . ., Inorganic Chemistry, vol. 16, No. 10, (1977), pp. 2538–2545.
Shibahara et al., Cubane-Type Mixed-Metal Clusters with . . ., Inorg. Chem. (1991), 30, 2693–2699.
Dedeian et al., Sulfur-Bridged Incomplete Cubane-Type . . ., Inorg. Chem. (1991), 30, 1687, 1688.
Nakata et al., Kinetic Studies on the Terminal-Ligand-Substitution . . ., Inorg. Chem. (1991), 30, 1575–1579.
Kim et al., The Cubane Structure of . . ., Inorg. Chem. (1991), 30, 574, 577.
Dimmock et al., Solution Studies on the Cuboidal Mixed-Metal Complex . . ., Inorg. Chem. (1990), 29 5120–5125.
Saito et al., Synthesis, Structure, and Electronic Properties of . . ., Inorg. Chem., 1989, 28, 3588–3592.
Richens et al., Crystal Structure of and Mechanism of . . ., Inorg. Chem., 1989, 28, 1394–1402.
Cotton et al., Synthesis and Structural Characterization of . . ., Inorg. Chem., 1989, 28, 2623–2630.
Ikari et al., A new Mixed Molybdenum-Tungsten . . ., Inorg. Chem., 1989, 28, 1248–1254.
Ikari et al., (µ-Ethylenediaminetetraacetato) . . ., Inorg. Chem., 1989, 28, 447–451.
Cotton et al., Derivatization of the Cuboidal . . ., Inorg. Chem., 1986, 25, 3529–3532.
Hogue et al., Chemistry of Polynuclear Metal Halides . . ., Inorganic Chem. vol. 9, No. 6, Jun. 1970, pp. 1354–1360.
Newton et al., Synthesis and Molecular Structure of . . ., Inorganic Chemistry, vol. 18, No. 6, 1979, pp. 1621–1626.
Blackmer et al., Conformational Dynamics of Dioxodi–µ–oxo–. . ., Inorganic Chemistry, vol. 15, No. 3, 1976, pp. 596–601.
Schrock et al., Preparation of W . . ., Inorg. Chem. 1983, 22, pp. 2801–2806.
Kathirgamanathan et al., Effect of Equivalent and Nonequivalent Sites . . ., Inorg. Chem. 1985, 24, 2950–2954.
Ooi et al., Substitution and Redox Properties . . ., Inorg. Chem. 1988, 27, 3626–3629.
Pan et al., Reactions of Tetrathiometalates, MS . . ., Inorg. Chem., 1984, 23, 4365–4269.
Shibahara et al., Double-Cubane-Type Molybdenum-Dulfur . . ., J. Am. Chem. Soc., 1987, 109, 3495–3496.
Cotton et al., The Mo . . ., J. Am Chem. Soc., 1985, 107, 6734–6735.
Halbert et al., Synthesis, Structure, and Reactivity of . . ., J. Am. Chem. Soc., 1984, 106, 1849–1851.
Shibahara et al., A Novel Cubane-Type . . ., J. Am. Chem. Soc., 1984, 789–791.

(List continued on next page.)

*Primary Examiner*—Gary E. Hollinden
*Attorney, Agent, or Firm*—Fish & Richardson

[57] ABSTRACT

The invention relates to the use as contrast enhancing agents in medical imaging, especially X-ray imaging, of multinuclear complexes, i.e. complexes, such as those of W2O2 (u2O)2, in which the complexed entity comprises at least two contrast enhancing atoms.

9 Claims, No Drawings

OTHER PUBLICATIONS

Weigel et al., Isonitrile Binding to a Site–Differentiated . . . , J. Am. Chem. Soc., 1990, 112, 8015–8023.

Hagen et al., Synthetic Routes to . . . , J. Am. Chem. Soc., 1983, 105, 3905–3913.

Martinez et al., Reaction Paths in the Formation of Triangular . . . , J. Am Chem. Soc., 1987, 109, 4615–4619.

Stack et al., Subsite–Differentiated Analogues of . . . , J. Am. Chem. Soc., 1988, 110, 2484–2494.

Shibahara et al., Structures and Properties of Cubane–type . . . , Inorganica Chemica Acta., 116 (1986) L25–L27.

Shibahara et al., Preparation of Tungsten(V) Aqua Ion . . . , Chemistry Letters, pp. 2327–2330, 1987.

Lee et al., Nonmolecular Metal Chalcogenide/halide Solids . . . Angew. Chem. Int. Ed. Engl. 29 (1990) 840–856.

Berry et al., Synthesis of Metal Molybdenum Tellurides . . . , J. Chem. Soc. Dalton Trans. 1991, pp. 57–59.

Drew et al., Dimeric Tungsten(V) Compounds containing . . . , J. Chem. Soc. Dalton Trans. 1987, pp. 1163–1167.

Wharton et al., Mechanism of the Oxidation of the Molybdenum . . . , J. C. S. Dalton, pp. 1526–1530 (1975).

Henkel et al., Preparation, Structure, and Properties of the Mo/Se Ions . . . , J. Chem. Soc., Chem. Commun., (1990), pp. 1014–1016.

Kathirgamanathan et al., Complete Synthesis of the Series of Triangular Oxo/Sulphido . . . , J. Chem. Soc. Commun., (1985), pp. 1437–1439.

Ooi et al., Solution Properties and Reactivity of the Aqua Ion of the . . . , Inorganic Chemistry, (1989), 28, 3799–3804.

Bino et al., A Trinuclear Molybdenum (IV) Cluster Compound . . . , Journal of the American Chemical Society, 100, Aug. 2, 1978, pp. 5252–5253.

Hollingshead et al., A Novel Oxyen–Centered Hexanuclear Molybdenum Alkoxide Cluster, . . . , J. Am. chem. Soc. 1990, 112, pp. 7402–7403.

Wasfi et al., Protonation–Induced Dynamic Stereochemistry of Hexafungstobis(organoarsonate) Anions, Journal of the American Chemical Society, 100, pp. 7786–7787, Nov. 22, 1978.

Cotton et al., The $Mo^3S^{4+}$ Aquo Ion, J. Am. Chem. Soc, 1985, 107, pp. 6734–6735.

Bunzey et al., Molybdenum Complexes of Aliphatic Thiols. Isolation and Characterization of Two Isomeric Forms . . . , Journal of the American Chemical Society, 99:12, Jun. 8, 1977, pp. 4168–4170.

Febin et al., Triangular Thiocomplexes of Molybdenum: Reactions with Halogens, Hydrohalogen Acids and Phosphines, Inorganic Chimica Acta, 167 (1990) pp. 39–45.

Hegetschweiler et al., A New Synthetic Pathway for . . . , Inorganica Chimica Acta, 169 (1990) pp. 235–243.

Shibahara et al., Preparation of the Incomplete Cubane–type . . . , Inorganica Chimica Acta, 113 (1986) L19–L21.

Cotton et al., A New Reaction Converting the . . . , Inorganica Chimica Acta, 102 (1985) L24–L27.

Mueller et al., Activation and Sulfur–Atom Transfer Reaction of Cluster–Bonded . . . , Agnew. Chem. Int. Ed. Engl. 19 (1980) No. 1, pp. 72–73.

Mueller et al., A Cluster With High Negative Charge and Cubane–Like . . . , Agnew. Chem. Int. Ed. Engl 21 (1982), No. 10, pp. 795–796.

Krespan, Functionalized Macroheterobicyclic Compounds, The Journal of Organic Chemistry, vol. 45, No. 7, pp. 1177–1180, Mar. 28, (1980).

Krespan, The Oxetane Function Spiro to Polyoxaaza Macroheterocycles, J. Org. Chem. vol. 40, No. 9, (1975) pp. 1205–1209.

Krespan, Macroheterocycles, The Oxetane Function Spiro to Macrocyclic Polyether Rings, J. Org. Chem., vol. 39, No. 16, (1974), pp. 2351–2355.

Campbell, Some Reactions of 3,3–Bis(choloromethyl)oxetane, Journal Organic Chemistry, Sep. (1957), vol. 22, pp. 1029–1035.

Tomohiro et al., Macrocyclic Tetranuclear Clusters with 28–, 32–, 36–, 40–, and 44–Membered Rings as High . . . , J. Chem. Soc. Dalton Trans., (1990), pp. 2459–2463.

Nasreldin et al., Kinetics of 1:1 NCS–for . . . , J. Chem. Soc. Dalton Trans. (1990), pp. 1765–1769.

Dimmock et al., Mechanism of the Reaction of Cuboidal . . . , J. Chem. Soc. Dalton Trans., (1990), pp. 3101–3106.

Shibahara et al., Preparation and Characterization of Dimeric Molybdenum (III)–Ethylene–diaminetetra–acetate Complexes, J. Chem. Soc., Dalton Trans., (1978), pp 95–99.

Kathirgamanathan et al., Complete Synthesis of the Series of Triangular Oxo/Sulphido Bridged . . . , J. Chem. Soc. Commun., 1985, pp. 1437–1439.

Kathirgamanathan et al., A Novel Electrochemical Method for the Preparation of Triangular and Cubic . . . , J. Chem. Soc. Chem. Commun., 1985, pp. 953–954.

Bandy et al., Synthesis, Crystal Structures, and Bonding of the Molybdenum Cubane . . . , J. Chem. Soc. Chem. Commun., (1983), pp. 1395–1397.

Mueller et al., Dissulfur Complexes, Coordination Chemistry Reviews, 46, (1982) pp. 245–280.

Shibahara et al., Preparation of Trinuclear Molybdenum (IV) Ion, . . . , Polyhedron, 5:357–361 (1986).

Day et al., Metal Oxide Chemistry in Solution: The Early Transition Metal Polyoxoanions, Science, vol. 228, No. 4699, May 3, (1985), pp. 533–541.

Fedorov et al., New Methods of Synthesising the Cluster Molybdenum Sulphide Halides . . . , Russian Journal of Inorganic Chemistry, 31 (10), (1986), pp. 1429–1431.

Barbaro et al., The Tetranuclear Trianion . . . , J. Am. Chem. Soc., (1990), 112, pp. 7238–7246.

MULTINUCLEAR COMPLEXES FOR X-RAY IMAGING

This application is a 371 of PCT/EP91/00587 filed on Mar. 27, 1991.

The present invention relates to the use in diagnostic imaging, in particular X-ray, ultrasound and scintigraphy of contrast agents comprising complexes of multinuclear moieties, and to contrast media containing such complexes.

All diagnostic imaging is based on the achievement of different signal levels from different structures within the body. Thus in X-ray imaging for example, for a given body structure to be visible in the image, the X-ray attenuation by that structure must differ from that of the surrounding tissues. The difference in signal between the body structure and its surroundings is frequently termed contrast and much effort has been devoted to means of enhancing contrast in diagnostic imaging since the greater the contrast between a body structure and its surroundings the higher the quality of the images and the greater their value to the physician performing the diagnosis. Moreover, the greater the contrast the smaller the body structures that may be visualized in the imaging procedure, i.e. increased contrast can lead to increased spatial resolution.

The diagnostic quality of images is strongly dependent on the inherent noise level in the imaging procedure—and the ratio of the contrast level to the noise level can thus be seen to represent an effective diagnostic quality factor for diagnostic images.

Achieving improvement in such a diagnostic quality factor has long been and still remains an important goal. In techniques such as X-ray and ultrasound, one approach to improving the diagnostic quality factor has been to introduce contrast enhancing materials, contrast agents, into the body region being imaged.

Thus in X-ray for example early examples of contrast agents were insoluble inorganic barium salts which enhanced X-ray attenuation in the body zones into which they distributed. More recently the field of X-ray contrast agents has been dominated by soluble iodine containing compounds such as those marketed by Nycomed AS under the trade names Omnipaque and Amipaque.

Much recent work on X-ray contrast agents has concentrated on aminopolycarboxylic acid (APCA) chelates of heavy metal ions and, recognising that effective imaging of many body sites requires localization at the body sites in question of relatively high concentrations of the metal ions, there have been suggestions that polychelants, that is substances possessing more than one separate chelant moiety, might be used to achieve this.

However we have now found that contrast enhancement may be achieved particularly effectively by the use of multinuclear complexes, that is complexes wherein the complexed moiety itself comprises two or more contrast enhancing atoms or for X-ray or ultrasound two or more heavy atoms.

For the sake of clarity, the word "atom" is used to refer to ionic and covalently bonded forms and not simply to isolated uncharged atoms. Moreover it will be understood that the complexed moiety, while it is polynuclear, is not so large as to be considered to be a particle itself. Thus it will generally have maximum dimensions of 80 Å or less, especially 40 Å or less.

Thus viewed from one aspect the invention provides a method of generating an image of a human or non-human animal, preferably mammalian, body which method comprises administering to said body a physiologically tolerable contrast enhancing amount of a multinuclear complex and generating an image of at least part of said body, e.g. by X-ray, ultrasound, or scintigraphy.

Viewed from a further aspect the invention also provides a multinuclear complex, especially a tungsten and/or molyblenum complex, for use as a diagnostic image contrast enhancing agent.

Viewed from a still further aspect the invention also provides a diagnostic imaging contrast medium comprising a multinuclear complex together with at least one sterile pharmaceutical carrier or excipient.

Viewed from another aspect the invention provides the use of a multinuclear complex for the manufacture of a contrast medium for use in imaging of the human or non-human animal body.

Multinuclear complexes have particular potential as contrast agents since, relative to mononuclear complexes such as the paramagnetic metal ion APCA chelates and polychelates conventionally proposed for use as X-ray contrast agents, the increase in the contrast enhancing atom content of the molecule is achieved with relatively little increase in the volume occupied by the contrast agent complexes, that is to say the use of multinuclear complexes enables a high ratio of contrast enhancing atom to overall complex volume to be achieved. Thus by increasing the relative content of contrast enhancing atoms in this way the total quantity of the contrast agent necessary in order to achieve the same contrast effect may be reduced and thus problems associated with contrast agent solubility or toxicity or with contrast medium viscosity may also be reduced.

The multinuclear complex used according to the invention may be ionic or, more preferably, may carry no net charge; most preferably the complex is non-ionic. Moreover it may be water-soluble or, less preferably, water-insoluble. Any necessary counterions should of course most preferably also be physiologically tolerable.

The range of physiologically acceptable counterions for therapeutically active agents is of course well known to pharmacologists.

Suitable counter cations include for example alkali and alkaline earth metal ions, e.g. sodium, calcium and magnesium and zinc, ammonium and organic amine cations, e.g. meglumine, alkylammonium, polyhydroxyalkylammonium, basic protonated amino acids, etc. Suitable counteranions include for example halide (e.g. chloride, bromide or iodide), sulphate, mesylate, phosphate, etc.

As mentioned above, by multinuclear it is meant that the complexed moiety should comprise two or more contrast enhancing atoms (preferably in the form of a molecular ion or ion groups). The multinuclear moiety may thus optionally contain further atoms which may have little or no contrast enhancing effect but which may for example function as bridging atoms bonding the contrast enhancing atoms together. Particularly suitable examples of bridging atoms include those of group VIb, e.g. oxygen, sulphur, selenium and tellurium, and substituted nitogen atoms. The use of selenium and tellurium, e.g. as bridging atoms, is especially attractive since the X-ray cross sections of these atoms, especially tellurium, are greater than those of the lower atomic weight sulphur, oxygen and nitrogen accordingly such atoms will contribute substantially to the overall X-ray attenuation by the complex.

Preferably the complexed multinuclear moiety will contain at least 2, for example up to 30, such as 2–15, e.g. 2 to 6, preferably 2 to 5 contrast enhancing atoms, particularly preferably 2, 3 or 4. The appropriate nature, e.g. the element, the isotope or the oxidation state, of the contrast enhancing atoms is of course dependent on the imaging technique in which the multinuclear complex is intended to function as a contrast agent. Thus for X-ray and ultrasound imaging the contrast enhancing atoms conveniently have atomic members of at least 37, preferably at least 50, and for scintigraphy the contrast enhancing atoms will be radioactive isotopes, e.g. radioactive metal ions.

For use as an X-ray contrast agent, it will generally be preferred that the multinuclear moiety should contain two or more heavy metal atoms, e.g. lanthanide, transition metal or other metal atoms such as for example Ce, Hg, Sr, Y, Zr, Tc, Ru, In, Ta, Nb, Dy, Hf, W, Mo, Re, Os, Pb, Ba, Bi, Ga, Sn and Tl, however Mo and W are particularly preferred. The choice of heavy metal used in the multinuclear complexes will be determined by a variety of factors including the toxicity of the overall complex and the X-ray absorption characteristics of the heavy atom. In this regard it should be noted that while the X-ray absorption cross section for atoms generally increases with increasing atomic nuber, the absorption cross section is itself dependent on the X-ray wavelength and increases with increasing photon energy until slightly above a value termed the K-edge whereafter attenuation decreases. Thus there are photon energy ranges for which one element is a better X-ray attenuator than a second even though outside these ranges the second element may be the better attenuator. Consequently the multinuclear complexes according to the invention will each have optimum photon energy ranges making them particularly suitable for operation with X-ray imaging apparatus utilizing X-rays having such photon energy ranges. However, by choosing multinuclear complexes containing atoms of more than one heavy element one may create X-ray contrast agents having optimal performance in more than one photon energy band or over a broader band. The complexes used according to the present invention are thus particularly attractive since they can be selected so as to match their X-ray attenuation profiles with the X-ray emission profiles of particular X-ray sources—in effect the invention provides "tunable" X-ray contrast media.

Non-chelant complexing agents, such as amines and carboxylic acids, e.g. acetic acid and amino acids, are known and may be used in the formation of the multinuclear complexes of the invention. However since many of the contrast enhancing multinuclear entities are extremely toxic it is clearly preferable that the formation constants of the multinuclear complexes should be as high as possible and accordingly it is particularly preferred that the multinuclear moiety should be bound in a chelate complex. Suitable chelant moieties will be discussed further below.

Many multinuclear complexes are known and attention is drawn for example to the following publications: Chisholm, Trans. Met. Chem. 3: 321 (1978); Lee et al., Ang. Chem. Intl. Ed. Eng. 29: 840–856 (1990); the Abstracts of the 5th International Conference on the Chemistry and Use of Molybdenum, 1985, page 133; Novak et al., J. Inorg. Nucl. Chem. 36: 1061–1065 (1974); Bürgi et al., Inorg. Chem. 20: 3829–3834 (1981); Chaudhuri et al., Z. anorg. allg. Chem. 521: 23–36 (1985); Ikari et al., Inorg. Chem. 29: 53–56 (1990); Tomohiro et al., J. Chem. Soc. Dalton Trans. 1990, 2459– 2463; Henkel et al., J. Chem. Soc. Dalton Trans. 1990, 1014–1016; Barbaro et al. JACS 112:7238–7246 (1990); Richens et al., Inorg. Chem. 28: 1394–1402 (1989); Saito et al., Inorg. Chem. 28: 3588–3592 (1989); J. Chem. Soc. Dalton Trans 1990, 1765–1769; Inorg. Chem. 27:3626–3629 (1988); JACS 108:2757–2758 (1986); and references cited therein. These multinuclear complexes generally fall into two categories, those in which the multinuclear moiety is bridged, that is to say where liganded metal atoms are bonded together via other atoms or ligands, and those where the moiety is unbridged, i.e. where the liganded metal atoms are bonded together directly. There is also a third general category in which the multinuclear moiety is apparently not bonded together, e.g. where two or more separate metal ions are complexed by the same chelant moiety.

Thus for example for the use of multinuclear complexes containing two liganded metal atoms (M) the main alternative structures are

(I)

and

(II)

where each M which may be the same or different is a metal atom; each L which may be the same or different is a ligand, either a molecule, an ion or one liganding moiety of a multidentate ligand; each B which may be the same or different is a bridging atom or ligand; and each m is an integer. Several L groups can of course be provided by one chelant and the metal atoms may be covalently bound to further atoms (generally designated by the letter A in the formulae referred to herein) not indicated by L or B and which function neither as ligands nor as bridges.

Where the M-B bonds to the bridging groups B of formula II are coordinate rather than covalent bonds, the multinuclear complex will be of the third general category referred to above. Examples of such complexes thus include the macrocyclic binuclear chelates such as

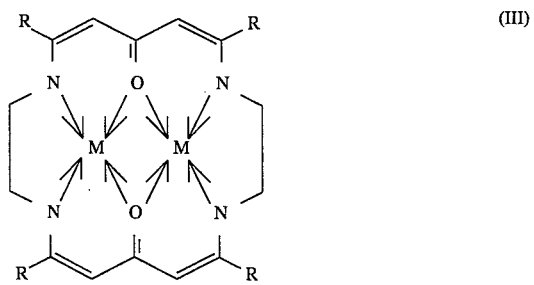

(III)

and

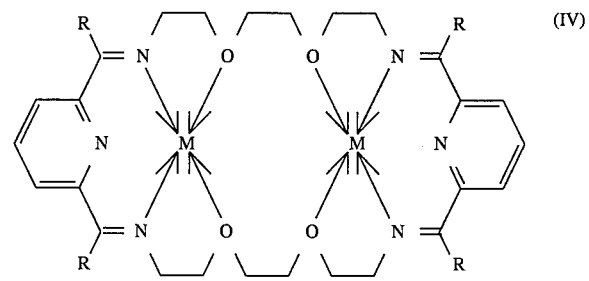

(IV)

where each R which may be same or different is hydrogen or an organic group and each M which may be the same or different is a metal atom or ion, e.g. Ni, Pb(II) or Cu(II).

Where the liganded metal atoms are directly bonded, the MM distances tend to be short and the multinuclear complexes are generally diamagnetic. Several complexes falling into this category are well known, e.g. compounds of formulae $$L_5M \equiv ML_5 \quad \text{(Ia)}$$

$$L_4M = ML_4 \quad \text{(Ib)}$$

(where each M which may be the same or different is for example Mo or Re).

While the use of multinuclear complexes wherein the liganded atoms are bonded directly together or are not linked by covalent bonds does fall within the scope of the invention, it is particularly preferred that the multinuclear complexes be of the bridged type wherein the liganded metal atoms are covalently linked via bridging atoms. Many such complexes are known and typical exemplary structures include the bi-, tri-, tetra- and hexa- nuclear structures of formulae II, V, VIII and IX

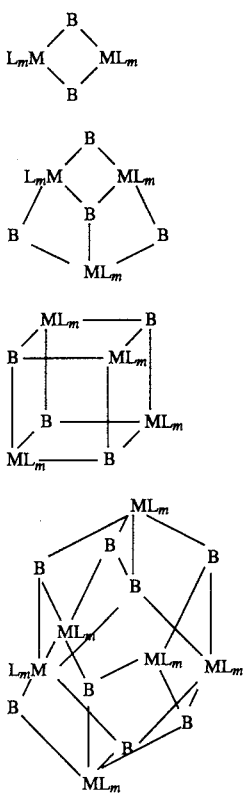

where each m which may be the same or different is an integer, each B which may be the same or different is a bridging atom and each M which may be the same or different is a metal, e.g. Mo, W, Re, or Tc, and where other non-bridging atoms covalently bonded to metals M are omitted for the sake of clarity. These bi, tri, tetra and hexanuclear clusters of formula $M_2B_2$, $M_3B_4$, $M_4B_4$, and $M_6B_8$ are well described in the literature, see for example J. Chem. Soc. A. 1970, 2421;
JCS Dalton Trans. 1975, 1526–1530;
Inorg. Chem. 16: 2538–2545 (1977);
JACS 99: 4168–4169 (1977);
J. Inorg. Nucl. Chem. 36: 1061–1065 (1974);
Inorg. Chem. 28: 447–451 (1989);
Chem. Letters, 1987, 2327–2330;
J. Chem. Soc. Dalton Trans., 1987, 1163–1167;
Inorg. Chem. 23: 4265–4269 (1984);
Inorg. Chem. 24: 2950–2952 (1985);
C. R. Seances Acad. Sci., Ser. C. 1966, 262, 1524;
JACS 106: 2710–2711 (1984);
J. Chem. Soc. Chem. Comm., 1985, 953;
JACS 107: 5565 (1985);
Inorg. Chem. 27: 3626–3629 (1988);
J. Chem. Soc. Dalton Trans., 1990, 1975–1769;
JACS 108: 2757–2758 (1986);
JACS 106: 789–791 (1984);
JACS 107: 6734–6735 (1985);
Inorg. Chim. Acta 116: L25–L27 (1986);
JACS 105: 3905–3913 (1983);
J. Chem. Soc. Chem. Comm., 1990, 1014–1016;
JACS 112: 7238–7246 (1990);
JACS 110: 1646–1647 (1988);
J. Chem. Soc. Dalton Trans., 1991, 51–59; and
Inorg. Chem. 28: 3588–3592 (1989).

The complexes above may be electrically charged or neutral—for administration as contrast agents they are however preferably complexed with ligands/chelating agents which serve to improve water solubility and to reduce toxicity and to leave unaffected, to only slightly increase or, most preferably, to reduce the magnitude of the overall electronic charge carried by the complex.

In the case of bridged structures of these four formulae, the structural formulae can conveniently be written $M_2L_q(\mu_2B)_2$ and $M_3L_r(\mu_3B)(\mu_2B)_3$, $M_4L_s(\mu_3B)_4$ and $M_6L_t(\mu_3B)_8$ respectively ($\mu_3B$ indicating that the B is a bridging atom bonded to 3 metals, and q, r, s and t respectively being integers identifying the total number of complexing moieties). As mentioned above, it is particularly preferred that the multinuclear complexes be chelate complexes and it is especially preferred that a single multidentate chelant be used to coordinate at least two and preferably all of the liganded centres. A multidentate chelant L coordinating for example three metals would be referred to in these formulae as $(\mu_3L)$.

Thus the multinuclear complexes used according to the invention preferably are compounds of the formula X $$(M_nB_uA_v)_xL_w \quad \text{(X)}$$

(where $M_nB_uA_v$ is a multinuclear entity; each M which may be the same or different is a metal atom covalently bonded to at least one, preferably 2–4, atoms; each B which may be the same or different is a bridging atom covalently bonded to at least two, preferably 2 or 3, atoms M; each A which may the same or different is a non-bridging atom covalently bonded to an atom M; each L which may be the same or different is a ligand, preferably a multidentate molecule or molecular ion, coordinately bonding to at least one atom M; n and u are positive integers of value 2 or greater; x and w are positive integers; and v is zero or a positive integer) or salts, especially physiologically tolerable salts, thereof.

In formula X above, n, u and v are preferably 2 to 30, especially 2 to 10, particularly 2 to 8; x is preferably 1 to 20, especially 1 to 10, and particularly 1. The value of w depends on the size and identity of the ligand—nonetheless w is preferably 1 or 2, especially 1.

Particularly preferred multinuclear complexes for use according to the invention include the APCA chelate complexes of mixed or non-mixed bi, tri, tetra and hexa nuclear oxides, sulphides, selenides and tellurides of molybdenum and/or tungsten, e.g. APCA chelates of multinuclear entities of formula

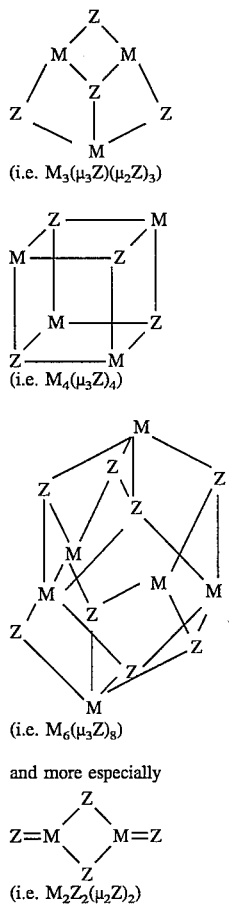

(i.e. $M_3(\mu_3 Z)(\mu_2 Z)_3$)

(i.e. $M_4(\mu_3 Z)_4$)

(i.e. $M_6(\mu_3 Z)_8$)

and more especially (i.e. $M_2 Z_2(\mu_2 Z)_2$) (VII)

where each M is independently W or Mo and each Z is independently O, S, Se or Te, e.g. $W_2S_2(\mu_2S)_2$, $W_2O_2(\mu_2O)(\mu_2S)$, $W_2O_2(\mu_2S)_2$, $MoWO_2(\mu_2O)_2$, $Mo_2O_2(\mu_2O)_2$, $Mo_2O_2(\mu_2S)_2$, $W_4(\mu_3S)_4$, $W_3(\mu_3S)(\mu_2S)_3$, $W_3(\mu_3Se)(\mu_2Se)_3$, $W_3(\mu_3Te)(\mu_2Te)_3$, $W_4(\mu_3Se)_4$, $W_4(\mu_3Te)_4$, $Mo_3(\mu_3Se)(\mu_2Se)_3$, $Mo_4(\mu_3Se)_4$, $Mo_2O_2(\mu_2Se)_2$, $Mo_3(\mu_3O)(\mu_3O)_3$, $W_2O_2(\mu_2O)_2$.

Many of these multinuclear clusters are known from the literature cited above—the others may be prepared using methods analogous to those described in the literature.

Particularly conveniently, such multinuclear entities are presented as their chelate complexes containing EDTA or other APCA's. Such chelate complexes are remarkably stable with regard to release of the heavy metal ions and thus $W_2O_2(\mu_2O)_2$ ($\mu_2$EDTA), for example, has been found to have a stability constant in aqueous solution of about 29.1 (see Novak et al., J. Inorg. Nucl. Chem. 36: 1061–1065 (1974)).

The structure of the $W_2O_4EDTA^{2-}$, or more preferably $[W(V)_2O_2(\mu_2O)(\mu_2EDTA)]^{2-}$, multinuclear complex has been suggested by Novak (supra) and others to have the structure

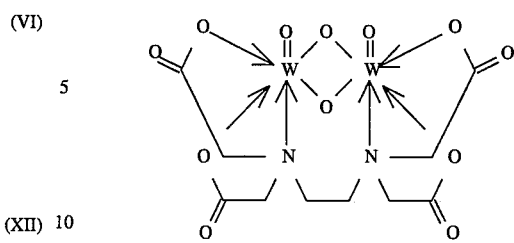

(XII)

Besides EDTA, other chelants are suitable for the preparation of the multinuclear chelate complexes used according to the invention.

It is particularly preferred that the electrical charge carried by the complexing moieties should substantially if not completely balance that carried by the complexed entity; for APCA chelants this may easily be achieved for example by omission, replacement or deactivation (e.g. by ester or amide formation) of one or more of the carboxyl moieties.

Many suitable chelants are widely known or have been described in the literature, especially literature relating to heavy metal detoxification agents bifunctional chelants and chelate-based contrast agents, e.g. those described in WO-A-89/00557 (Berg) and the documents mentioned therein and in the search report appended thereto, U.S. Pat. No. 4,647,447 (Gries), U.S. Pat. No. 4,826,673 (Dean), EP-A-230893 (Felder), EP-A-217577 (Frincke), U.S. Pat. No. 4,652,519 (Warshawsky), U.S. Pat. No. 4,687,659 (Quay), and numerous other recent patent publications of Nycomed AS, Salutar Inc, Schering AG, Squibb, Bracco, Mallinckrodt, Dow and Guerbet.

The chelants useful for complexing the multinuclear moeity can be selected from a wide range of structures. Many of the most useful chelants are of general formula XIII $$Z'(X(CHR_1)_a)_b XZ' \qquad (XIII)$$

(where a is an integer of from 2 to 12, preferably 2 to 10, e.g. 2, 3, or 4; b is an integer of from 1 to 8, preferably 2, 3 or 4;

each R, independently is hydrogen, a hydrophilic or linking group (e.g. a hydroxyalkyl group) or two groups $R_1$, or one $R_1$ and one group Z', together represent a saturated or unsaturated heterocyclic or carbocyclic ring, preferably with 5–7 ring atoms;

each X independently is O, S, NZ' or PZ', each Z' indpendently is hydrogen, hydroxyalkyl, mercaptoalkyl, carboxyalkyl (or an amide or ester derivative thereof e.g. —$CH_2CONHCH_3$) or optionally hydroxy or mercapto substituted acyl, or is a side chain $((CHR_1)_a X^*)_c Z^*$ (where c is 1 to 4 and $X^*$ and $Z^*$ are as form a briding group $((CHR_1)_a X^*)_c (CHR_1)_a)$ or are salts defined for $X^*$ and $Z^*$ but do not represent any group containing a $X^*$ or $Z^*$ group) or two groups Z' together thereof.

While polyamines, especially linear or cyclic polyamines, such as ethylenediamine,1,4,7-triazacyclononane and cyclen, can be used as chelants, in general APCAs are preferred, particularly DTPA, EDTA and derivatives thereof and other cyclic and non-cyclic APCAs as defined in WO-A-89/00557 and APCAs of formula XIV

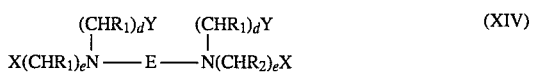

(XIV)

where each $R_1$ is independently hydrogen or an optionally hydroxylated and/or alkoxylated alkyl group or an organic side chain adapted for the attachment of or attached to a macromolecule;

d and e each is an integer having a value of 1, 2 or 3;

each X is independently a group COOH or a derivative thereof;

each Y is independently a group X, $SR_1$, $OR_1$ or $N(R_3)_2$;

E is a group $(CHR_2)_f(X''(CHR_2)_f)_g$ where f is an integer of from 2 to 5, preferably 2 or 3, g is zero, 1 or 2, preferably zero or 1, each f preferably being 2 when g is non-zero, X" is O, S or $N(CHR_1)_dY$, preferably O or S, each $R_2$ is independently $R_1$ or, when the carbon to which it is attached is not bonded to a nitrogen, hydroxyl, or two $R_2$ groups, especially where f is 2, may together with the intervening carbons form a cycloalkyl group optionally substituted by hydroxyl or $R_1$ groups, and each $R_3$ is independently a group $R_1$ or $N(R_3)_2$ represents a preferably saturated heterocyclic group preferably having 5 or 6 ring members, optionally containing as a further heteroatom a nitrogen or oxygen and optionally substituted by $R_1$ groups.

In the chelants of formula XIII or XIV, any alkyl moiety preferably has a carbon atom content of up to 8, any cycloalkyl group preferably is a $C_{3-8}$, especially $C_{5-7}$, ring and any carboxyl derivative is preferably a $CON(R_3)_2$ or $CON(OH)R_1$ group.

Examples of suitable chelants include compounds of formulae:

and the phosphorus analogues of these nitrogen-donor based ligands.

For $M_4B_4$ multinuclear complexes, e.g. $W_4(\mu_3B)_4^{4+}$ (where B=S, Se, Te, O, N—$R^{31}$ or P—$R^{31}$ (where $R^{31}$ is an appropriate substituent, e.g. hydrogen, aryl (e.g. phenyl), alkyl etc.), chelants (i) to (vii) (where z= 1) are of particular interest; for $M_3B_4$ complexes, e.g. $W_3(\mu_3B')(\mu_2B'')_3^{4+}$ (where B' and B" are S, Se, Te, O, $NR^{31}$ or $PR^{31}$ B' preferably being S) chelants (vii) (where z= o) and (viii) to (xv) are of particular interest; and for $M_6B_8$ complexes, e.g. $W_6(\mu_3S)_8$, chelants such as (xvi) to (xx) are of particular interest. For $M_2B_2$ complexes, e.f. $W_2O_2(\mu_2O)_2^{2+}$ chelants such as NTA, IDA, EDTA, HEDTA, DTPA, DTPA-BMA, HEDDA, TTDA, EDTA-BMA, TBEDDA, MEEDDA, TTHA, EDDA, EHPG, PDTA, CHDTA, HPDTA and tri-azacyclononane monoacetic acid, especially PDTA and EDTA, are of particular interest.

For $M_4B_4$ and $M_3B_4$ multinuclear complexes, the use of macrocyclic chelants, e.g. those of formula (vii) is particularly preferred as a means by which to enhance solution stability.

Particularly preferred chelants include cyclen, EDTA, DTPA, DOTA, DO3A, HP-DO3A, the 6-oxa and 6-thia analogues of DTPA and amides thereof, e.g. DTPA-BMA and DTPA-BMO (6-carboxymethyl-3,9-bis(morpholinocarbonylmethyl)- 3,6,9-triazaundecanedioic acid—the Gd(III) chelate whereof is sometimes referred to as gadopenamide).

Where the chelant is to be attached to a macromolecule, this may conveniently be any tissue, organ or cell targeting macromolecule, for example a biomolecule such as a pro-

| | |
|---|---|
| $(HOOCCH_2)_2NCH_2CH_2N(CH_2COOH)_2$ | (i) |
| $(HSCH_2CH_2)_2NCH_2CH_2N(CH_2CH_2SH)_2$ | (ii) |
| $H_2NCH_2CH_2N(CH_2COOH)CH_2CH_2N(CH_2COOH)CH_2CH_2NH_2$ | (iii) |
| $H_2NCH_2CH_2N(CH_2CH_2SH)CH_2CH_2N(CH_2CH_2SH)CH_2CH_2NH_2$ | (iv) |
| $HOOCCH_2(NCH_2CH_2)_3NCH_2COOH$ | (v) |
| $HSCH_2CH_2(NCH_2CH_2)_4SH$ | (vi) |

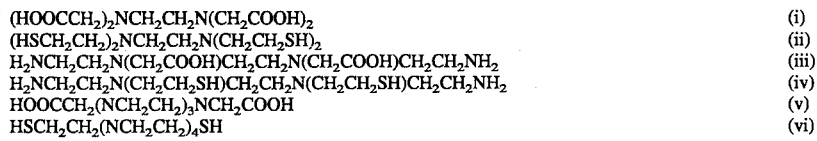

(vii)

(where y = 6,7,8,9 or 10
and z = 0 or 1)

| | |
|---|---|
| $(HOOCCH_2)_2NH$ | (viii) |
| $(HSCH_2CH_2)_2NH$ | (ix) |
| $(HOOCCH_2)_2NCH_2CH_2N(CH_2COOH)CH_2CH_2N(CH_2COOH)CH_2CH_2N(CH_2COOH)_2$ | (x) |
| $(HSCH_2CH_2)_2NCH_2CH_2N(CH_2CH_2SH)CH_2CH_2N(CH_2CH_2SH)CH_2CH_2N(CH_2CH_2SH)_2$ | (xi) |
| $(HOOCCH_2)_2N(CH_2CH_2NH)_2CH_2CH_2N(CH_2COOH)_2$ | (xii) |
| $(HSCH_2CH_2)_2N(CH_2CH_2NH)_2CH_2CH_2N(CH_2CH_2SH)_2$ | (xiii) |
| pyridine-2,6-dicarboxylic acid | (xiv) |
| 2,6-bis-merceptomethyl-pyridine | (xv) |

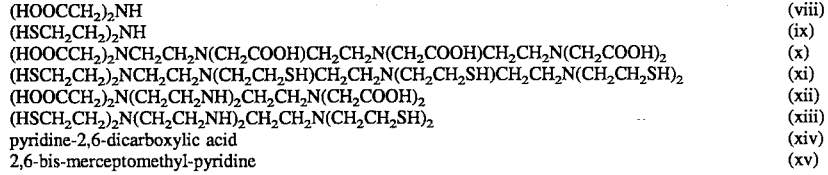

(xvi)    (xvii)    (xviii)

| | |
|---|---|
| tetra-N-alkyl-ethylenediamine | (xix) |
| penta-N-alkyl-diethylenetriamine | (xx) | tein, an antibody or antibody fragment, or alternatively it may be a biologically relatively inert material such as a polysaccharide or poly-sugar alcohol, e.g. dextran or starch. Such macromolecules are discussed extensively in the recent literature relating to contrast agents.

The chelants of formulae XIII and XIV are already known from the literature or may be prepared in analogous fashion to the known chelants. The preparation of chelants of formula XIII and XIV will however generally fall into one of two categories: derivatization of a polyamine or amination of polyfunctional compounds. Derivatization can be performed in one or more stages and the groups introduced may, in intermediate or final stages, be subject to reduction or deprotection steps.

Thus for example starting from the linear polyamine

$$NH_2-E'-NH_2 \quad (XV)$$

(where E' is $(CHR_2)_f[X'''(CHR_2)_f]_g$ and X''' is O, S or NH) derivatization may be effected by the following nonreductive or reductive reaction schemes:

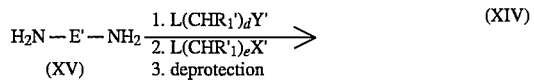

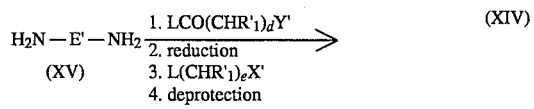

where L is a leaving group and $R_1'$, Y' and X' are optionally protected $R_1$, Y and X groups.

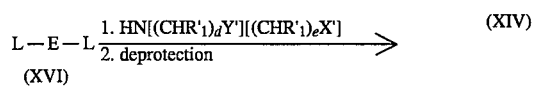

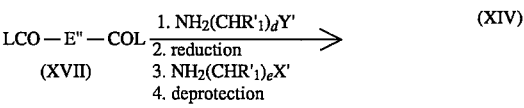

where E'' is $(CHR'_1)_{f-h}[Z'(CHR_1')]_{j}i[Z'(CHR'_1)_{f-1}]_j$ (where j is 0 or 1, h+j is 2, i is zero or the positive integer g-l) and L, $R'_1$, Y' and X' are as hereinbefore defined.

The polyamine starting materials are either available commercially or may be prepared by routine methods. Thus for example commercially suitable polyamines include $NH_2(CH_2)_{2-5}NH_2$, $NH_2(CH_2)_2O(CH_2)_2NH_2$, $NH_2CH_2CHOHCH_2NH_2$, $NH_2(CH)_2S(CH_2)_2NH_2$. Optionally substituted polyamines may also be prepared by methods described in or analogous to those of EP-A-287465 (Schaeffer), WO-A-89/00557 (Berg), Brechbiel et al. Inorg. Chem. 25: 2772 (1986), Yeh et al. Analytical Biochem. 100: 152 (1979), Vögtle et al. Liebigs Ann. Chem. (1977) 1344, Kasina et al. J. Med. Chem. 29: 1933 (1986), Bedell et al. Inorg. Chem. 21:874 ( 1982 ), etc.

Derivatization of the polyamines may be effected using alkylation agents such as those described by EP-A- 230893 (Felder), e.g. HalCH$_2$COL", HalCH(COOH)CH$_2$O Benzyl, or HalCH(COOH)$_2$ (where Hal is Cl or Br and L" is OH, NHAlkyl or NAlkyl$_2$ (e.g NHCH$_3$ or N(CH$_3$)$_2$) or HalCH$_2$NAlkyl$_2$ (e.g. ClCH$_2$N(CH$_3$)$_2$), followed where necessary by deprotection of protected groups. Examples of such schemes include

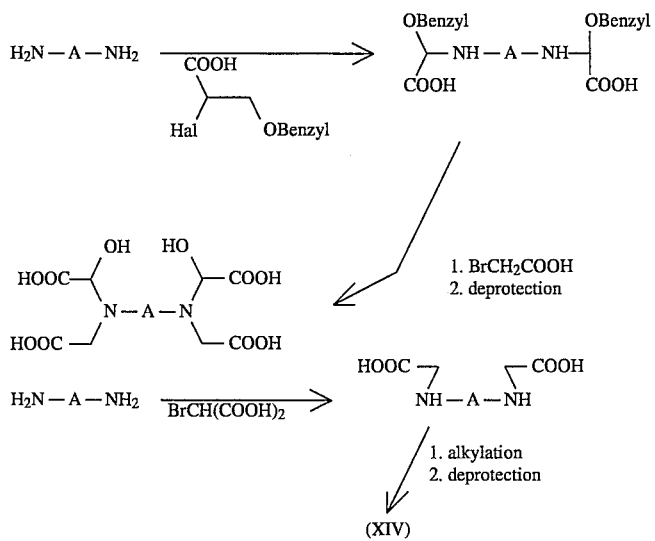

Alternatively a bifunctional reagent of formulae

$$L-E-L \quad (XVI)$$

or $$LCO.E''.CO.L \quad (XVII)$$

may be aminated with or without a subsequent reduction step according to the following schemes:

Selective alkylation of amines is described by Nordlander et al. Tetr. Lett. (1978) 4987 and J. Org. Chem. 49: 133 (1984) and by Aspinall et al. JACS 63: (1941). Many other appropriate derivatization procedures are described in the literature.

For the reductive procedure discussed above, reaction may be of many of the same or similar polyamines with aldehyde, carboxyl or carboxyl derivative compounds followed by reduction of the amide carbonyl groups, e.g. using sodium cyanoborohydride or diborane, e.g. as in the scheme

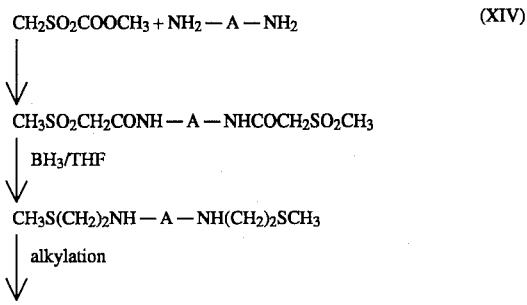

The resulting thioesters could equally be produced by reaction of an aminocarboxylic acid reagent with a chloroalkylsulphide, e.g.

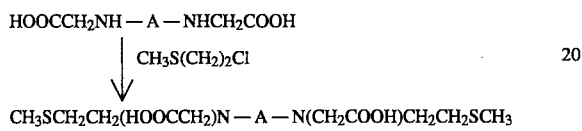

As mentioned above, the chelants of formula (XIV) can also be produced by amination of polyfunctional reagents. One example of this procedure is given by Huber et al. J. Chem. Soc. Chem. Comm. (1989) 879, i.e.

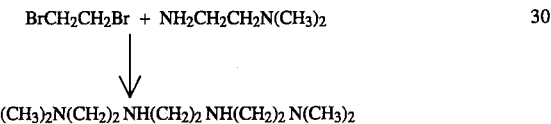

The resulting polyamine can then be converted to a compound of formula XIV by reaction with $HOCH_2CN$ followed by hydrolysis. A wide variety of other polyhalo and amine compounds suitable for use in such reactions are available commercially or may be prepared using text book methods.

In a similar manner, polyfunctional acids may be reacted with appropriate amines if necessary after activation of the acid groups, reduction of the amide and alkylation will yield chelants of formula XIV. Commercially available polyfunctional acids utilizable in this way include for example

HOOCBCOOH where B is , $-(CHOH)_2-$, $-(CH_2)_{1-3}-$ or

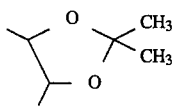

In order to attach the chelant to a macromolecule, e.g. a protein or a carbohydrate, the chelant may be provided with a reactive side chain (e.g. described by Meares et al. Anal. Biochem. 142: 68(1984), etc). Alternatively attachment can be efected for example using the methods developed by Salutar Inc. (See for example WO-A-90/12050 and Sieving et al., Bioconjugate Chem. 1: 65–71 (1990)) or the mixed anhydride or cyclic anhydride methods of Krejcarek et al Biochemical and Biophysical Research Comm. 77: 881 (1977) or Hnatowich et al. Science 220: 613 (1983) etc. Attachment of the chelant may be either directly to the macromolecule or, preferably, to a an intermediate polymer, e.g. poly-L-lysine or polyethylene-imine, onto which a plurality of chelants may be loaded, e.g. as discussed in EP-A-331616 (Deutsch).

Thus for example the following macromolecule-linkable chelants are suggested in the literature:

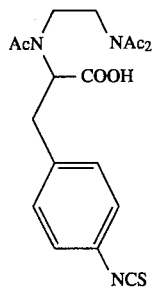

(Westerberg et al. J.
Med. Chem. 32: 736
(1989))
(Ac=$CH_2COOH$)

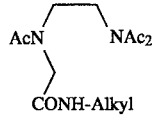

(JACS 59: S+D 10
(1982))

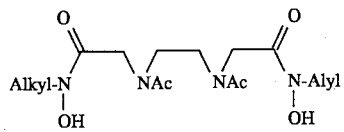

(Turowski et al.
Inorg. Chem. 27: 474
(1988))

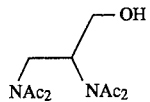

(Hernandez et al. An.
Quim. Ser. B. 83: 172
(1987))

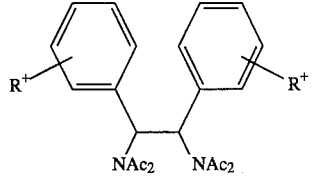

($R^+$ = $NO_2$, OH)

(Zupanc et al. Glas.
Hem Technol. Bosne
Hercegovine (1970)71)

-continued

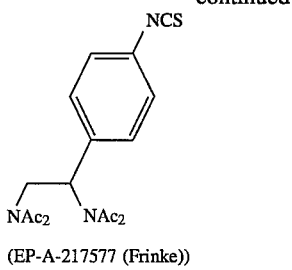

(EP-A-217577 (Frinke))

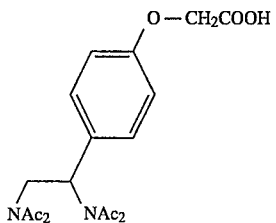

(J. Radiol. Chem. 53: 327 (1979))

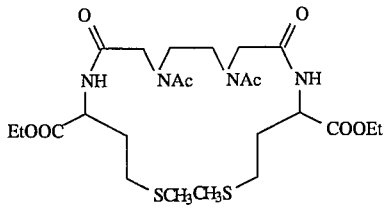

(Bulman et al. Inorg. Chem. 26: 2483 (1987))

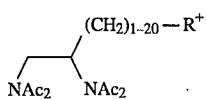

($R^+$ = COOH, $NH_2$, CHO)

(US-A-4632519 (Warshawsky))

The tridentate tris-thiols of Holm et al. (see JACS 112: 8015–8023 (1990) and JACS 110: 2484–2494 (1988)) also deserve particular mention, especially for the complexation of tetranuclear clusters.

The multinuclear complexes used according to the invention may be prepared by the methods suggested in the literature or by analogous methods. In particular, novel complexes may be prepared from known complexes by ligand interchange.

Thus, for example for tungsten based multinuclear entities as mentioned above, oxalatotungstate(V) may be used as a starting material and ligand exchange reactions with calcium chelates of APCAs to precipitate out calcium oxalate may be carried out. Chromatographic isolation and purification methods, such as suggested by Ikari (supra) appear particularly suitable.

The preparation of an intermediate oxalate may be avoided by use of other literature known methods, e.g. the electrochemical reduction suggested by Baba et al. Mem. Fac. Tech. Tokyo Metropolitan Univ. 32: 3207 (1982).

Other preparative techniques that deserve particular mention include the oxidation of tungstate complexes with the addition of the desired chelant/complexant as suggested by Chaudhuri (supra) and the reduction of tungstates with reductants and a chelant/complexant (which may have oxidative or reductive properties) as suggested by Lozano et al. in Polyhedron 31: 25–29 (1984).

Further examples of synthetic routes by which the multinuclear complexes used according to the invention may be prepared include:

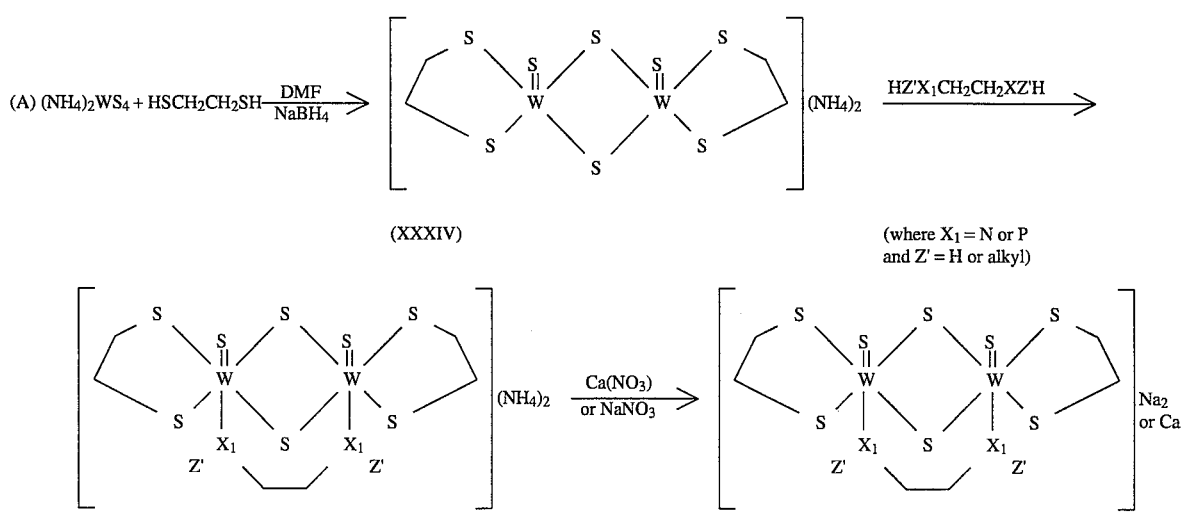

-continued (B) $(NH_4)WS_4$ + $HX_2CH_2CH_2X_1CH_2CH_2X_1CH_2CH_2X_2H$  $\xrightarrow{\text{DMF}}{\text{NaBH}_4}$ 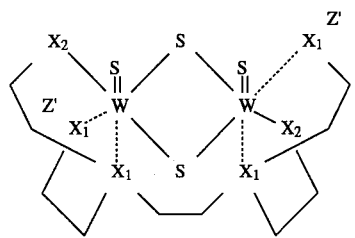

$Z'_2X_1CH_2CH_2$   $CH_2CH_2X_1Z'_2$ (XX)

(where $X_1$ = N or P
$X_2$ = O or S
and $Z'$ = H or alkyl)

(C) $W_3(\mu_3S)(\mu_2S)_3{}^{4+}$ + (XX) $\longrightarrow$ 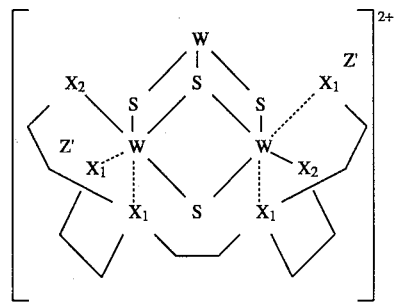 $\xrightarrow{HX_2CH_2CH_2X_1Z'CH_2CH_2X_2H}$ (where $X_1$, $X_2$ and $Z'$
are as in (A) above)

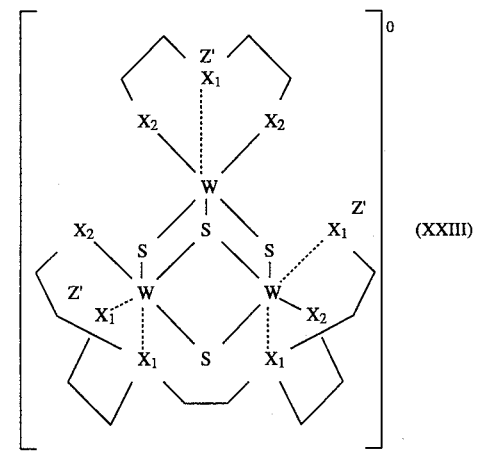 (XXIII)

Molybdenum and tungsten trinuclear aqua complexes $[M_3(\mu_3B)(\mu_2B)_3(H_2O)_9]^{4+}$ (where M is Mo or W and B is O or S) can be prepared by methods known from the literature. The co-ordinated waters in these complexes can readily be replaced by chelants xvi to xx to reduce toxicity. Single or mixed ligand combinations may be used to produce ionic or non-ionic complexes.

(D) $W_3(\mu_3S)(\mu_2S)_3{}^{4+}$ + EDTA $\longrightarrow$

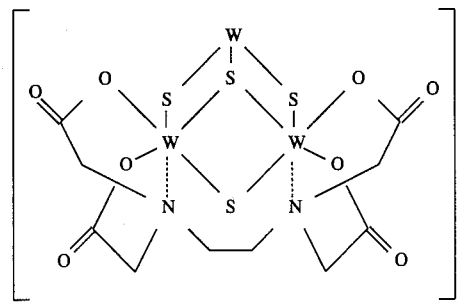 $\xrightarrow{Z'_2X_1CH_2CH_2X_1Z'CH_2CH_2X_1Z'_2}$ (where $X_1$ and $Z'$ are as
in (A) above)

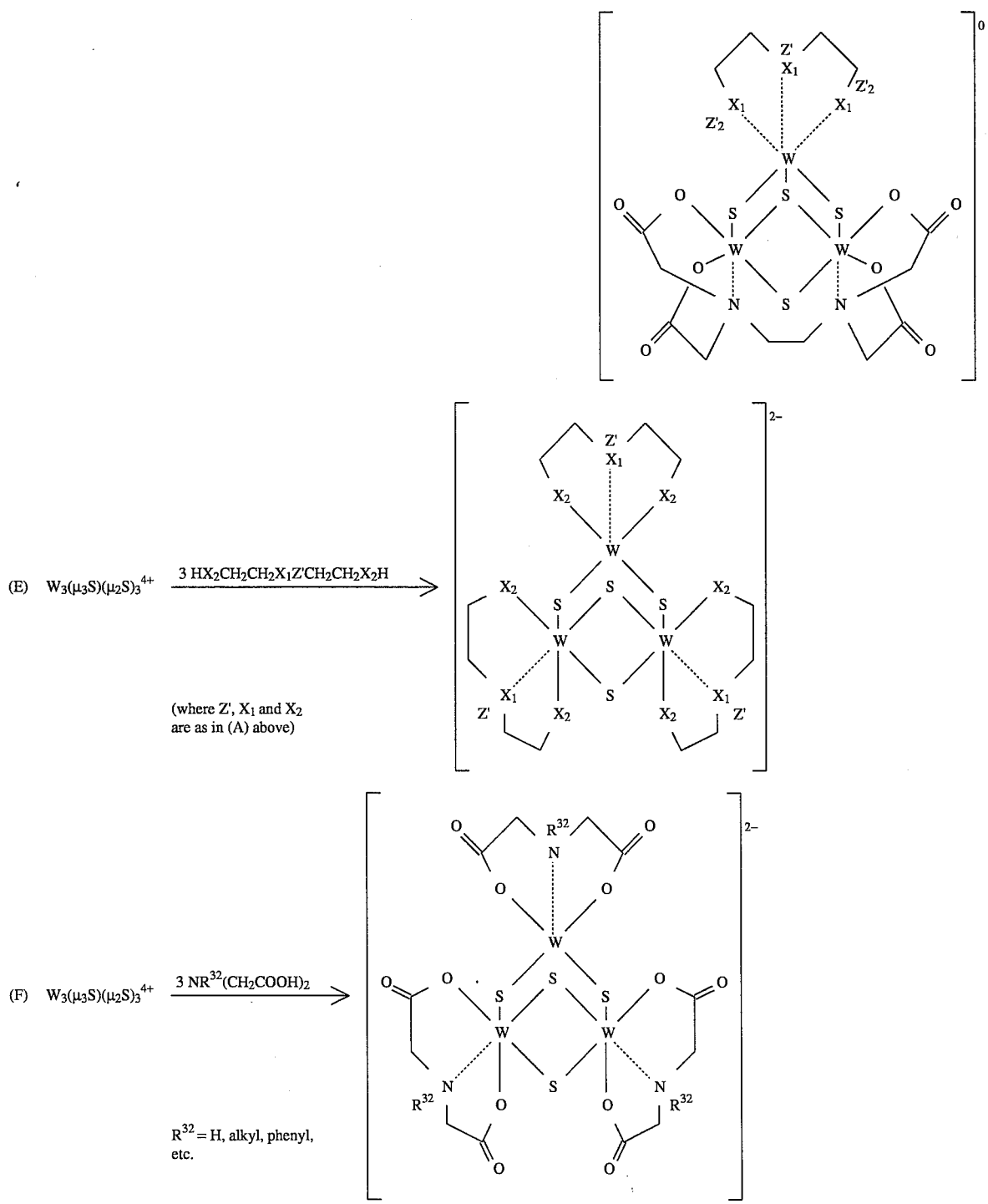

(G) $W_3(\mu_3S)(\mu_2S)_3^{4+}$ + [N(COCH$_2$C(CH$_3$)$_2$SH)—(CH$_2$)$_k$]$_3$ →
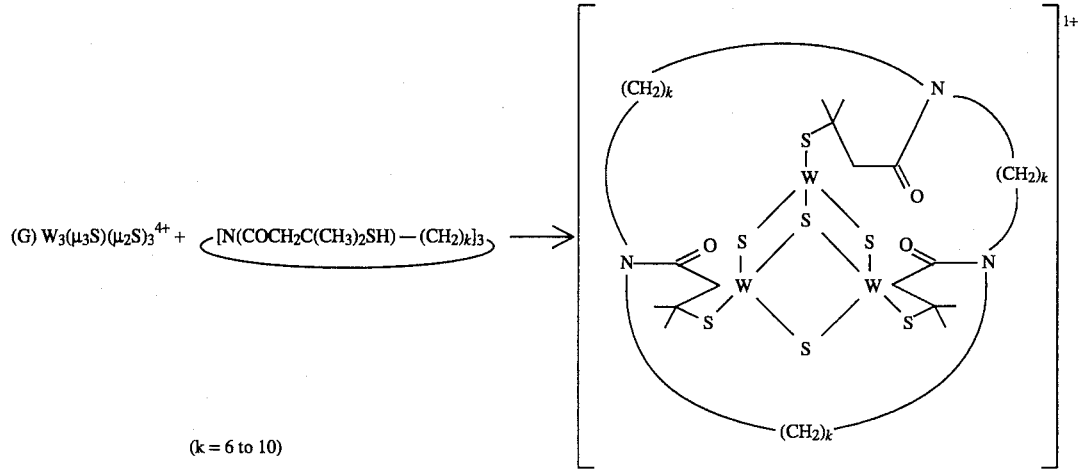
(k = 6 to 10)
The coordinated water in the tetranuclear aquacomplexes may be substituted by ligands such as chelants i to vii to reduce toxicity. Selected examples are shown below.
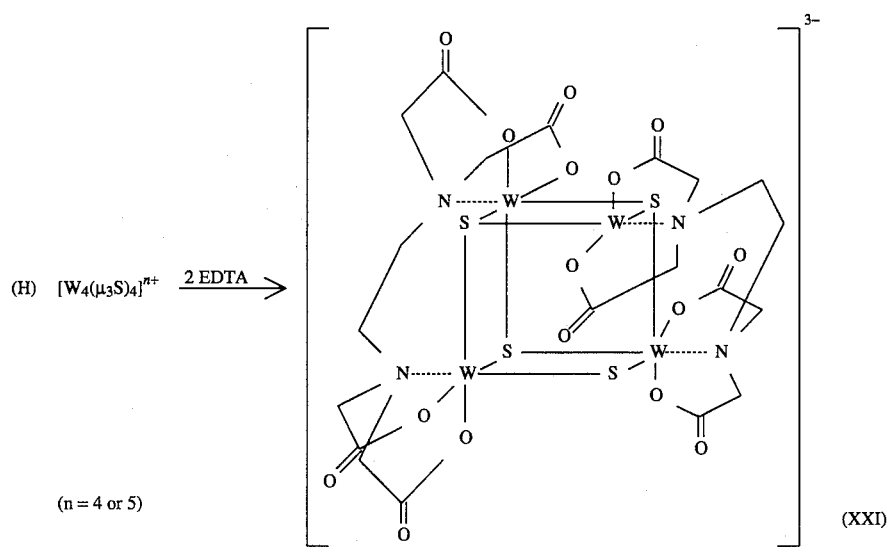
(H) $[W_4(\mu_3S)_4]^{n+}$ $\xrightarrow{\text{2 EDTA}}$
(n = 4 or 5)
(XXI)
(I) $2.W_2O_2(\mu_2S)_2(\mu EDTA)$ $\xrightarrow{\text{NaBH}_4, \text{Zn/Hg or Na}_2S_2O_4}$ (XXI)

(J) $[W_4(\mu_3S)_4]^{n+}$ + (XX) ⟶

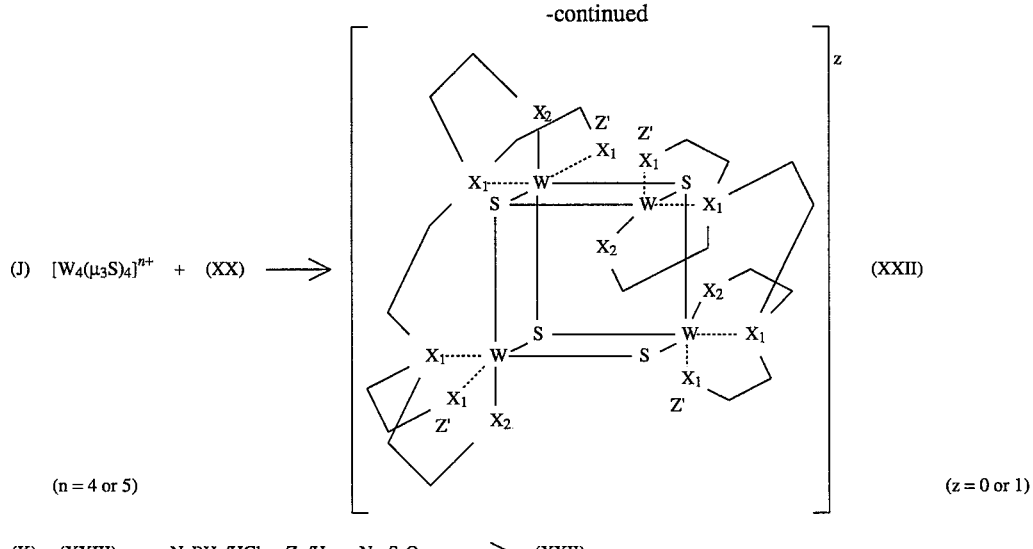

(n = 4 or 5)    (XXII)    (z = 0 or 1)

(K) (XXIII) + NaBH$_4$/HCl or Zn/Hg or Na$_2$S$_2$O$_4$ ⟶ (XXII)

(L) $[W_4(\mu_3S)_4]^{n+}$ + [N(COCH$_2$C(CH$_3$)$_2$SH)—(CH$_2$)$_k$—]$_4$ ⟶

(where k = 6±10)

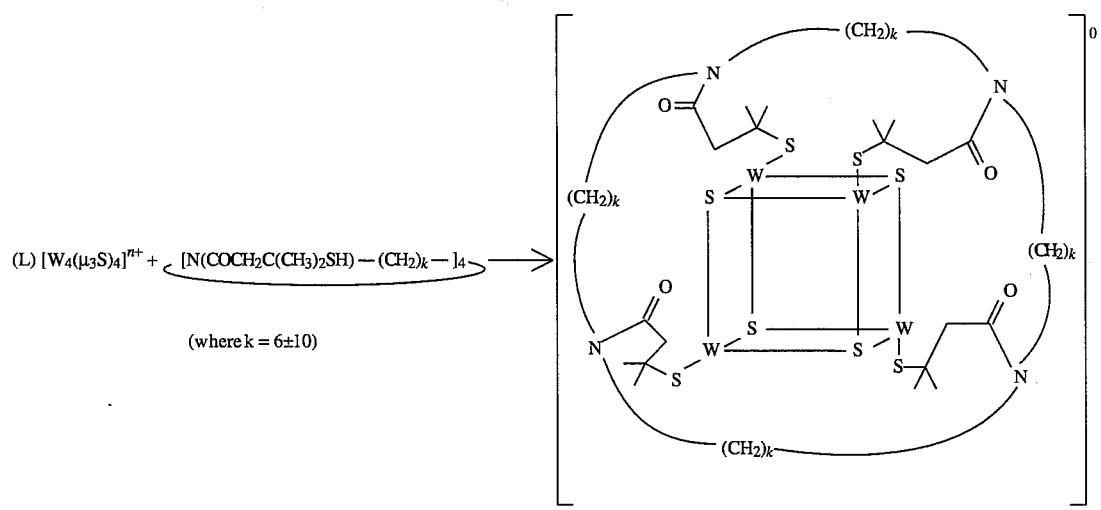

Molybdenum and tungsten based tetranuclear aqua complexes $(M_4(\mu_3B)_4(H_2O)_{12})^{n+}$ (where M=W or Mo, B=S or Se and n=4 or 5) can be prepared by various chemical and electrochemical procedures. Tetranuclear tungsten complexes may also be prepared by reduction of binuclear complexes, e.g. using reductants such as NaBH$_4$, Na$_2$S$_2$O$_4$ and Zn/Hg amalgam and the compound of formula XXIV, by photoirradition of tungsten hexacarbonyl and sodium sulphide in methanol, or of a mixture of a trinuclear complex and tungsten hexacarbonyl in methanol or reaction of a trinuclear complex and the W(III) aquoion under reducing conditions with heat or photo-irradition.

For adminstration to human or animal subjects, the multinuclear complexes will conveniently be formulated together with pharmaceutical or veterinary carriers or excipient. The contrast media of the invention may conveniently contain pharmaceutical or veterinary formulation aids, for example stabilizers, antioxidants, osmolality adjusting agents, buffers, pH adjusting agents, colorants, flavours, viscosity adjusting agents and the like. They may be in forms suitable for parenteral or enteral administration, for example, injection or infusion or adminstration directly into a body cavity having an external voidance duct, for example the gastrointestinal tract, the bladder and the uterus. Thus the media of the invention may be in conventional pharmaceutical adminstration forms such as tablets, coated tablets, capsules, powders, solutions, suspensions, dispersions, syrups, suppositories etc; solutions, suspensions and dispersions in physiologically acceptable carrier media, e.g. water for injections, will however generally be preferred. Where the medium is formulated for parenteral administration, the carrier medium incorporating the multinuclear complex is preferably isotonic or somewhat hypertonic. Moreover, media for parenteral administration will preferably contain small quantities, e.g. 0.01 to 10 mole percent relative to the multinuclear complex of free chelants or of weak chelate complexes with physiologically tolerable chelated species (e.g. Ca$^{2+}$); small additions of sodium or calcium salts may also advantageously be made.

For use as X-ray contrast media, the media of the invention should generally have a heavy atom content of 1 millimole/l to 5 mole/l, preferably 0.1 to 2 mole/l. Dosages of from 0.5 to 1.5 mmoles/kg will generally be sufficient to provide adequate contrast although dosages of 0.8 to 1.2 mmoles/kg will normally be preferred.

For scintigraphy, dosages of the radioactive species will generally be lower.

Thus in summary the present invention provides a particularly effective means by which contrast media efficiency may be enhanced by increasing the relative proportion of molecular volume that is occupied by the contrast enhancing heavy or paramagnetic metal atom. For X-ray contrast media in particular, this also enables higher K- edge value atoms than the iodine of the now conventional X-ray contrast media to be utilized effectively.

The present invention will now be illustrated further by the following non-limiting Examples (all ratios and percentages are by weight and all temperatures are in degrees Celsius unless specified otherwise):

EXAMPLE 1

Bis(μ-oxo)(μ-ethylenediaminotetraaceto-N,N')bis(oxotungstate(V)), disodium salt
$Na_2[W_2O_2(\mu_2O)_2(\mu_2EDTA)]$ Alternative A:

The potassium salt (37 g, 65 mmol) of the oxalato complex of tungsten(V) (prepared according to Collenberg, Z. Anorg. Allg. Chem. 102: 247–276 (1918)), sodium acetate (60 g, 441 mmol) and ethylenediaminetetraacetic acid (10 g, 34 mmol) were dissolved in oxygen free water (800 ml) and warmed to 80°–90° C. under nitrogen. Degassed warm calcium acetate solution (1M, 150 ml) was added with stirring and the mixture was allowed to cool. After filtering off the precipitate, degassed barium acetate solution (1M, 40 ml) was added. A small amount of the immediate precipitate was filtered off and the filtrate was concentrated in vacuo. The residue was collected on a filter, washed with water and dried. This material (18.1 g, 21 mmol barium-complex) was dissolved in warm oxygen free water (2000 ml) and sodium sulfate solution (1M, 25 ml) was added. The mixture was allowed to cool, filtered and concentrated to dryness. The residue was taken up with water (50 ml) and precipitated by successive addition of ethanol.

Yield: 15.17 g (30 %) of the sodium salt of tungsten-EDTA complex.

Purification of 10 g by HPLC afforded the title compounds of Example 1 (3 g) and Example 2 (4.25 g)

$^1$H-NMR was as reported by Ikari et al., Inorg. Chem. 28: 1248–1254 (1989).

Alternative B:

The potassium salt (0.10 g, 0,062 mmol) of the oxalato complex of tungsten(V) (prepared according to Baba et al., Mem. Fac. Tech. Tokyo Metropolitan Univ. 32: 3207–3220 (1982)), ethylenediaminetetraacetic acid (0.028 g, 0.124 mmol) and sodium acetate (0.021 g, 0.25 mmol) were dissolved under nitrogen in oxygen free water (1.5 ml) and heated to 100 ° C. Calcium chloride dihydrate (0.046 g, 0.31 mmol) dissolved in oxygen free water (2 ml) was added and the mixture allowed to cool. After filtering off the precipitate, barium hydroxide (0.043 g, 0.136 mmol), dissolved in water (2 ml), at pH 4 (acetic acid) was added. The mixture was concentrated in vacuo to near dryness, the precipitate collected by centrifugation, washed with two drops of water and dried in vacuo over $P_2O_5$.

Yield: 0,044 g (21%) of the barium salt of the complex.

This was dissolved in water (20 ml) with heating, sodium sulfate (0,017 g, 0.05 mmol) dissolved in water (2 ml) was added and the precipitate removed by centrifugation. Concentration of the clear solution to dryness gave the title compound quantitatively. HPLC-analysis showed the product to be identical with that prepared by alternative A.

EXAMPLE 2

(μ-Ethylenediaminotetraaceto-N,N')(μ-oxo)(μ-sulphido)bis(oxotungstate(V)), disodium salt
$Na_2[W_2O_2(\mu_2O)(\mu_2S)(\mu_2EDTA)]$ The potassium salt (37 g, 65 mmol) of the oxalato complex of tungsten(V) (prepared according to Collenberg, Z. Anorg. Allg. Chem. 102: 247–276 (1918)), sodium acetate (60 g, 441 mmol) and ethylenediaminetetraacetic acid (10 g, 34 mmol) were dissolved in oxygen free water (800 ml) and warmed to 80°–90° C. under nitrogen. Degassed warm 1M calcium acetate solution (150 ml) was added with stirring and the mixture was allowed to cool. After filtering off the precipitate, degassed 1M barium acetate solution (40 ml) was added. A small amount of immediate precipitate was filtered off and the filtrate was concentrated in vacuo. The residue was collected on a filter, washed with water and dried.

This material (18.1 g, 21 mmol barium - complex) was dissolved in warm oxygen free water (2000 ml) and 1M sodium sulfate solution (25 ml) was added. The mixture was allowed to cool, filtered and concentrated to dryness. The residue was taken up with water (50 ml) and precipitated by successive addition of ethanol.

Yield 15.17 g (30 %) of the sodium salt of tungsten-EDTA complex.

Purification of 10 g crude material by HPLC afforded 4.25 g of the title compound.

$^1$H-NMR was as reported by Ikari et al., Inorg. Chem. 28: 447–451 (1989).

EXAMPLE 3

Bis(μ-sulphido)(μ-ethylenediaminotetraaceto-N,N')bis(oxotungstate(V)) disodium salt
$Na_2[W_2O_2(\mu_2S)_2(\mu_2EDTA)]$ Alternative A The title compound is prepared and purified according to the procedure of Shibahara et al., $37^{th}$ Nat. Conf. Coord. Chem., Tokyo, Abstr. 1AP06.

Alternative B 1 g of $(NH_2)_2WS_4$ (2.87 mmol) was dissolved in 20 ml of $H_2O$ to give a yellow suspension. 1 g of $NaBH_4$ on alumina and 10 ml of 6M HCl were alternatively added to the yellow suspension. An immediate dark-brown suspension was formed, which was then heated at 120° C. under an $O_2$ stream for 15 hours. After cooling the resulting mixture to ambient temperature, a green solid was removed by filtration. The red-brown filtrate was treated with 0.6 g of $Na_4EDTA$. After the pH of the mixture was adjusted to 1.2, it was heated at 100° C. for 1 hour. Some precipitate was observed during this heating period. After removing the solid by filtration, the yellow-orange filtrate was cooled and left at ambient temperature for 4 days, giving orange crystals. The crystals were washed with a small amount of methanol and then dried in the air. The yield was 0.20 g.

The mass spectral data of this product showed the molecular ions at 791 and 753 corresponding to the mass of $K[W_2O_2S_2(EDTA)]$ and $[W_2O_2S_2(EDTA)]+H$, respectively. $^1$H NMR resonances in $D_2O$ were found at 2.54 ppm(s, 4H), 3.14 ppm(d, 2H, J=16.4 Hz), 3.40 ppm(d, 2H, J=17. Hz) and 3.52 ppm(d, 4H J=17.1 Hz).

EXAMPLE 4

Bis($\mu$-oxo)($\mu$-ethylenediaminotetraaceto-N,N')(oxomolybdenum(V)) (oxotungstate(V)), disodiumsalt
$Na_2[MoWO_2(\mu_2O)_2(\mu_2EDTA)]$ The title compound is prepared and purified according to the procedure of Ikari et al. Inorg. Chem. 28: 1248–1254 (1989).

EXAMPLE 5

Preparation of a solution containing the disodium salt of bis($\mu$-oxo)($\mu$-ethylenediaminotetraaceto-N,N')bis(oxotungstate(V))

The salt from Example 1 (2.95 g, 3.85 mmol) was dissolved in water (18 ml) and the pH was adjusted to 7 by careful addition of 1M sodium hydroxide. Water was added to 20 ml, the solution passed through a 0.22 $\mu$m sterile filter and placed into four 5 ml vials. The solution contained 0.20 mmol of the disodium salt of bis($\mu$-oxo)($\mu$-ethylenediaminotetraaceto-N,N' )bis(oxotungstate(V)) per ml. The $LD_{50}$ in mice was found to be 10–14 mmol/kg.

EXAMPLE 6

Preparation of a solution containing the disodium salt of ($\mu$-ethylenediaminotetraaceto-N,N')($\mu$-oxo)($\mu$-sulphido)bis(oxotungstate(V))

The salt from Example 2 (2.66 g, 3.40 mmol) was dissolved in water (17 ml) and the pH was adjusted to 7.0 by careful addition of 1 M sodium hydroxide. The solution was passed through a 0.45 $\mu$m filter into four 5 ml vials.
The solution contained 0.19 mmol of the disodium salt of ($\mu$-ethylenediaminotetraaceto-N,N')($\mu$-oxo)($\mu$-sulphido)bis(oxotungstate(V)) per ml. The $LD_{50}$ in mice was found to be approx. 10 mmol/kg.

EXAMPLE 7

Preparation of a solution containing the disodium salt of bis($\mu$-sulphido)($\mu$-ethylenediaminotetraaceto-N,N')bis(oxotungstate(V))

The salt from Example 3 (2.00 g, 2.5 mmol) is dissolved in water (12.5 ml) and the pH is adjusted to 7.0 by careful addition of 1M sodium hydroxide. The solution is filtered into three 5 ml vials.

EXAMPLE 8

Preparation of a solution containing the disodium salt of bis($\mu$-oxo)($\mu$-ethylenediaminotetraaceto-N,N')(oxomolybdenum(V)) (oxotungstate(V))

The salt from Example 4 (2.00 g, 2.95 mmol) is dissolved in water (14.7 ml) and the pH is adjusted to 7.0 by careful addition of 1M sodium hydroxide. The solution is filtered into three 5 ml vials.

EXAMPLE 9

Bis($\mu$-oxo)($\mu$-N,N'-propylenediaminetetraacetato)bis(oxotungstate(V)), barium salt
$Ba[W_2O_2(\mu_2O)_2(\mu_2EDTA)]$ The potassium salt (1.61 g, 1 mmol) of the oxalato complex of tungsten(V) (prepared according to Baba et al., Mem. Fac. Tech. Tokyo Metropolitan Univ. 32: 3207– 3220 (1982)) and 1,2-diaminopropane-N,N,N',N'-tetraacetic acid (0.612 g, 2 mmol) were dissolved under nitrogen in a mixture of 50 ml oxygen-free water and sodium acetate-solution (1M, 8 ml) and heated to 100° C. Calcium acetate-solution (1M, 10 ml) was added with stirring and the mixture allowed to cool. After filtering off the precipitate, a barium acetate-solution (1M, 2 ml) was added, the solution was filtered and the title compound was precipitated by dropwise addition of ethanol. It was collected on a filter, washed with 50% aqueous methanol and dried in vacuo at 40° C. Yield: 0.413 g (43%) of the pentahydrate.

EXAMPLE 10

Bis($\mu$-oxo)($\mu$-N,N'-propylenediaminetetraacetato)bis(oxotungstate(V)), sodium salt
$Na[W_2O_2(\mu_2O)_2(\mu_2EDTA)]$ The title compound is prepared by dissolving the barium salt of Example 9 in warm water. After addition of a stoichiometric amount of a 1M sodium sulfate solution the mixture is allowed to cool, filtered and the filtrate concentrated to dryness.

EXAMPLE 11

The title compound was prepared by a slightly modified version of the procedure described in JACS 108:2757–2758 (1986).

3 g of $(NH_4)_2WS_4$ (8.62 mmol) was dissolved in 75 ml of water to give a yellow solution. 3 g of $NaBH_4$ and 30 ml of concentrated HCl were added alternatively to the tungsten solution. Upon this addition, an immediate color change from yellow to dark brown was observed. The resulting brown suspension was heated at 100° C. for 2 hours After cooling the mixture, it was filtered to remove a dark brown solid and to obtain a brown filtrate. The brown solution was loaded on a Sephadex G-15 column, which resulted in a brown band on top of the column. After a 5-day air oxidation of the brown band, it was eluted with 2M HCl solution. The second purple fraction ($\lambda$max=570 nm and 320 nm) was collected and evaporated to dryness under high vacuum at 36°–40° C., which gave dark grey solid. The product was washed with acetone and dried in the air. The yield was 0.506 g (0.62 mmol, 22%).

The mass spectral data in dithiothrietol(DTT)/dithioerythrietol matrix gives a molecular ion at 1139 equivalent to the mass of $[W_3S_4(DTT)_3]$+2H.

The elemental analysis indicated that the product was $W_3S_4(H_2O)_9Cl_4$ and contained 2.4% HCl and 3.9% $H_2O$.
Calculated: W(52.53%), S(12.22%), Cl(15.86%). Found: W(52.46%), S(12.24%), Cl(15.96%).

EXAMPLE 12

$[N(C_2H_5)_4][W_2S_2(\mu-S)_2(EDT)_2]$

This compound was prepared according to a literature procedure. (Inorg. Chem. 23: 4265–4269 (1984)). 0.81 g (2.3 mmol) of $(NH_4)_2WS_4$ was added to 25 ml of $N_2$-saturated DMF. The resulting mixture was a greenish-yellow suspension. After adding 0.3 ml (3.6 mmol) of 1,2-ethanedithiol (EDT), a bright yellow color formed. The reaction mixture was heated under a $N_2$ flow at 120° C. in an oil bath for 2 hours. After several minutes of heating, the solution become red-orange. At the end of the reaction period, a brownish red suspension was noted, 0.63 g of $N(C_2H_5)_4Cl$ was then added to the cooled suspension at ambient temperature. 20 ml of diethyl ether was added to precipitate the product. Brownish red crystals were recovered by filtration and washed with methanol and then with ether. The addition of more ether (150 ml) to the red-orange filtrate gave more product. All the fractions were then combined and recrystallized once from methanol. The total yield of the product was 0.75 g (1.6 mmol, 69% from $(NH_4)_2[WS_4]$).

The mass spectral data of this product showed a molecular ion at 681 corresponding to $W_2S_4(EDT)_2+H$.

We claim:

1. A sterile X-ray contrast medium comprising at least one pharmaceutical carrier or excipient together with a physiologically tolerable multinuclear tungsten complex of the formula $$(W_3B_uA_v)_xL_w,$$

wherein $W_3B_uA_v$ is a multinuclear entity; each tungsten atom of which is covalently bonded to at least one atom B; each B of which may be the same or different and is a bridging atom covalently bonded to at least two tungsten atoms; each A of which may be the same or different and is a non-bridging atom covalently bonded to a tungsten atom; each L of which may be the same or different and is a ligand coordinately bonded to at least one tungsten atom; u is a positive integer of value 2 or greater; x and w are positive integers; and v is zero or a positive integer, or a physiologically tolerable salt of said tungsten complex.

2. A medium as claimed in claim 1 where each A and B is O, S, Se, Te or a protonated or substituted nitrogen or phosphorus atom.

3. A medium as claimed in claim 2 wherein the multinuclear entity comprises a unit of formula $W_3(\mu_3B)(\mu B)_3$ wherein each B is O, S, Se, Te or a protonated or substituted nitrogen or phosphorus atom.

4. A medium as claimed in claim 3 wherein said chelant is an aminopolycarboxylic acid or an ester or amide thereof or is a macrocyclic polyacylated polyamine.

5. A medium as claimed in claim 1 further comprising a free chelant or a physiologically tolerable salt or a weak complex thereof with a physiologically tolerable metal ion.

6. In a method of generating contrast-enhanced X-ray images of a subject comprising administering to said subject an X-ray attenuating amount of a physiologically tolerable sterile X-ray contrast agent and generating an X-ray image of said subject, the improvement comprising administering as said contrast agent a compound having an anion comprising a bridging atom cluster $W_3B_b$, each B is independently an oxygen or sulfur atom, each W is bound to at least two B atoms, each B atom is bound to at least two W atoms, and b is an integer having a value of at least two.

7. A method as claimed in claim 6 wherein said cluster is a $W_3B_4$ cluster.

8. A method as claimed in claim 6 wherein said anion is complexed by a ligand.

9. A method as claimed in claim 8 wherein said ligand is an aminopolycarboxylic acid.

* * * * *